United States Patent [19]
Moreau

[11] 3,985,020
[45] Oct. 12, 1976

[54] OIL POLLUTION COMPLIANCE MONITOR

[75] Inventor: James O. Moreau, Denville, N.J.

[73] Assignee: Exxon Research and Engineering Company, Linden, N.J.

[22] Filed: July 14, 1975

[21] Appl. No.: 595,881

[52] U.S. Cl. .............................. 73/61.1 R; 73/198
[51] Int. Cl.² ................... G01N 15/00; G01N 33/18
[58] Field of Search ............... 73/61.1 R, 61 R, 28, 73/198, 195

[56] References Cited
UNITED STATES PATENTS

| | | |
|---|---|---|
| 1,445,770 | 2/1923 | Kendall .............................. 73/61 R |
| 3,167,949 | 2/1965 | Stenzel et al. .................... 73/61.1 R |
| 3,612,887 | 10/1971 | Canevari et al. ............... 73/61.1 R X |

*Primary Examiner*—James J. Gill
*Attorney, Agent, or Firm*—F. Donald Paris

[57] ABSTRACT

A monitoring system for proving compliance with pollution (e.g. oil) regulations, which in a preferred embodiment enables a tanker to prove that restrictions on total oil or rate of oil pollution have not been violated. The system comprises adsorbing an oil sample which is proportional to total oil discharged and rate of oil discharged on a continuously moving lipophilic belt and subsequently analyzing the belt after the voyage has been terminated when required to prove that the tanker has not exceeded ocean pollution requirements.

22 Claims, 10 Drawing Figures

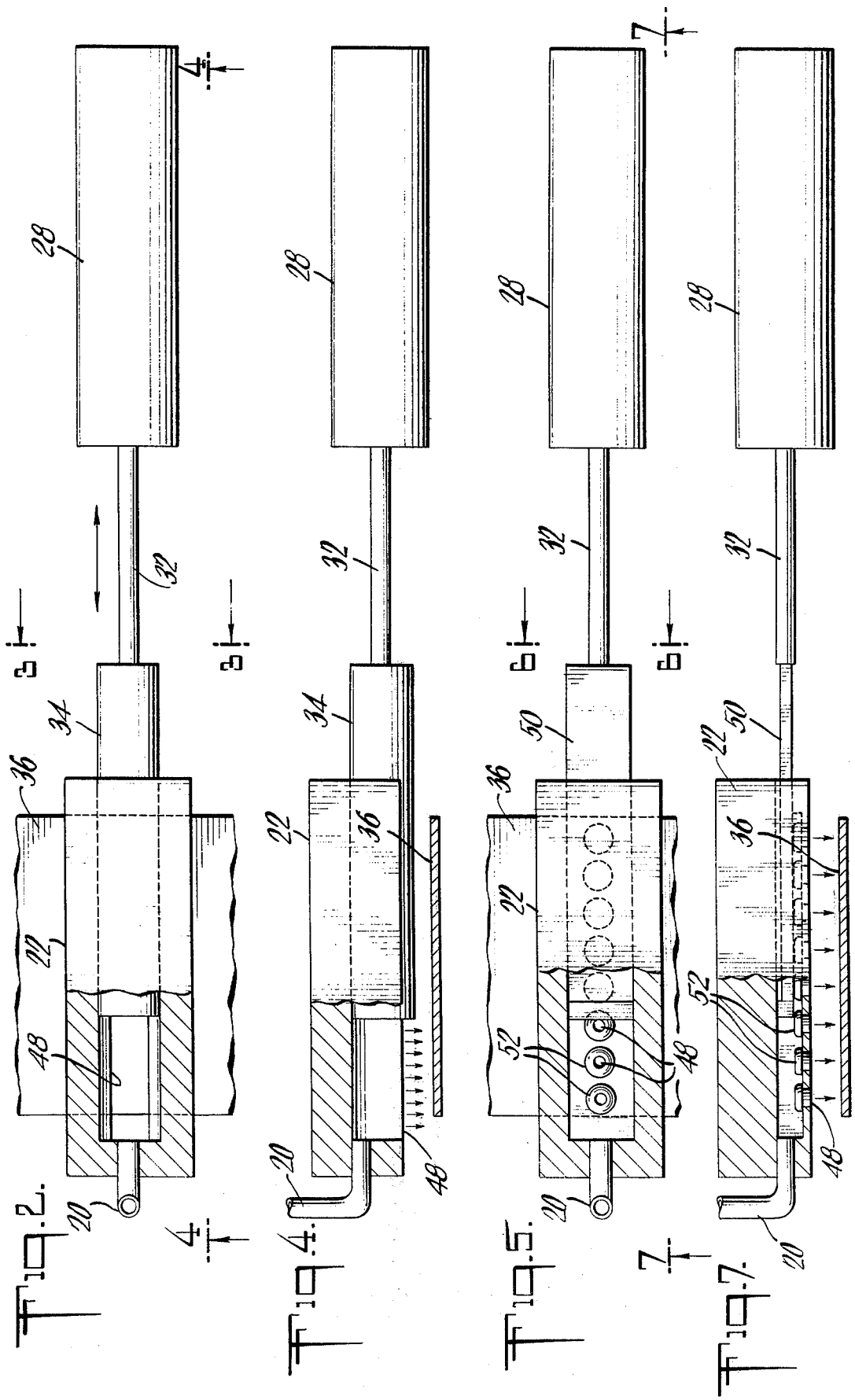

OIL POLLUTION COMPLIANCE MONITOR

BACKGROUND OF THE INVENTION

Proposed international regulations in the oil pollution area contemplate limiting both the total oil and the rate of oil which can be discharged by a tanker into the ocean. It is likely that these regulations may further require that the tanker be able to prove that it has not discharged oil in the ocean above the prescribed limits. This would require a single device or system to enable the tanker to prove compliance both with total and rate limitations on oil discharges.

It has previously been demonstrated that lipophilic material is feasible for use in adsorbing oil from an oily water stream, and further has been shown that lipophilic material can be analyzed to determine oil concentration, for example, see U.S. Pat. No. 3,612,887, or the Salwico Oil Content Monitor, Salen & Wicander, Sweden, or API Publication No. 4172, 1973, pages 139–144, by Schatzberg and Jackson. None of these prior art devices, however, are capable of monitoring both total oil and rate of oil discharged in an oily water stream. Other prior art disclosures of general interest for measuring oil in water are U.S. Pat. Nos. 3,133,437; 3,167,949; and 3,385,108. These techniques, however, are not capable of measuring low concentrations of oil in water such as may be discharged from a tanker.

SUMMARY OF THE INVENTION

The present invention provides an oil pollution compliance monitor which satisfies the needs heretofore stated, by providing a system which makes it possible to measure not only low oil concentrations, but also to determine rate of oil discharged and/or total volume of oil discharged during a tanker's voyage. According to the present invention, the monitor comprises a sample manifold for contacting an oil absorbing tape with a sample from the oil discharge stream, such that oil concentration, the rate of oil discharged and the total volume of oil discharged can be directly determined from analysis of the tape. The present invention has the primary technical advantage of enabling important measurements to be made which heretofore were not possible. A further advantage of this invention in a preferred embodiment is its simplicity of design, which makes it possible for the monitor to operate exclusively with pneumatic power sources thereby permitting installation in an already hazardous environment such as a tanker pump room. The simplicity of the present monitor also offers the potential for operation within a tamperproof locked box, which could provide compliance proof that would be acceptable in an international court of law before an international body.

The monitor basically comprises a belt of lipophilic tape which is pulled from a supply reel at a constant speed through or beneath a manifold which holds an oil water sample and dispenses the sample into contact with the tape as it passes below. The tape is collected and stored on a suitable takeup reel which may be properly stored to minimize deleterious effects of vaporization, oxidation and biodegradation of the oil. As the oily sample water is directed into contact with the tape passing below the sampling manifold, the width of the tape which is contacted can be adjusted in proportion to the flow rate of the ballast being discharged.

Thus, it is apparent that the present invention provides an oil pollution compliance monitor with advantages and features which have not heretofore been obtainable or provided by the prior art. Having in mind the foregoing objects that will be evident from an understanding of this disclosure, the invention comprises the combination, arrangements, and devices and methods as demonstrated in the presently preferred embodiment of the invention which is hereinafter set forth in such detail as to enable those skilled in the art readily to understand the function, operation, construction and advantages of it when read in conjunction with the accompanying drawings.

BRIEF DESCRIPTION OF THE DRAWINGS

FIG. 2 is an enlarged top view of the sample manifold and positioner of FIG. 1;

FIG. 4 is a side view taken substantially on the line 4—4 in FIG. 2;

FIG. 6 is an end view taken substantially on the line 6—6 in FIG. 5;

FIG. 7 is a side view taken substantially on the line 7—7 in FIG. 5;

DESCRIPTION OF THE PREFERRED EMBODIMENT

Figure 1:
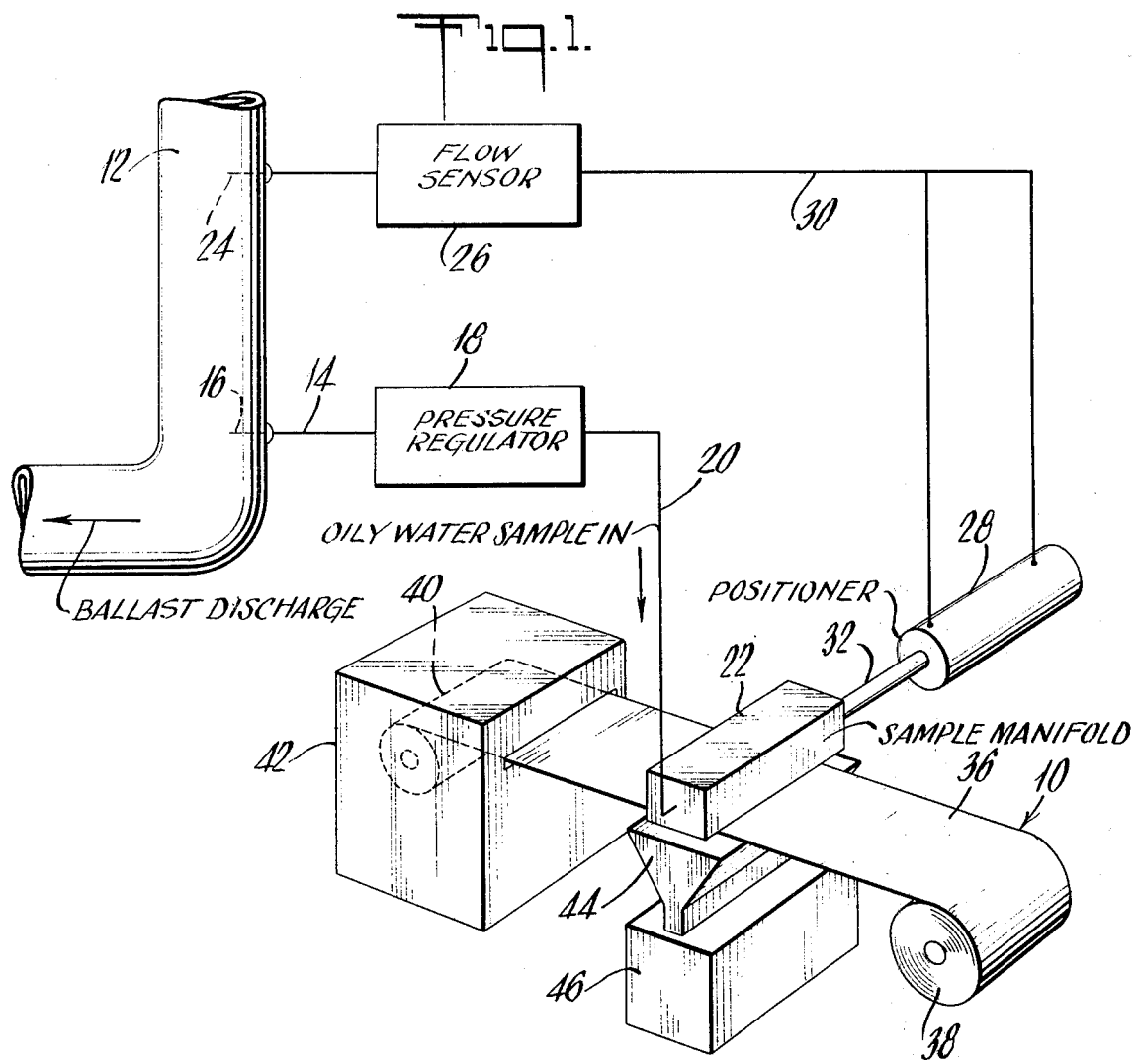
FIG. 1 is a schematic perspective view of a preferred embodiment of the present invention comprising an oil pollution compliance monitor operably connected with a ballast discharge line for receiving an oily water sample therefrom.
Figure 3:
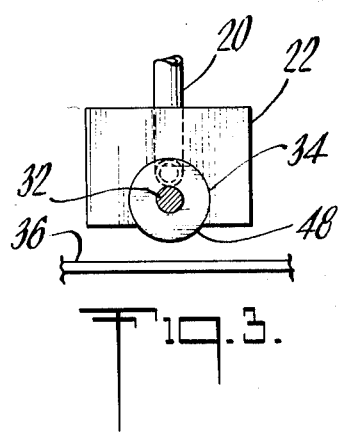
FIG. 3 is an end view taken substantially on the line 3—3 in FIG. 2.

Referring now to the drawings wherein like parts are designated by the same reference numeral throughout the several views, there is shown in FIG. 1 an oil pollution compliance monitor 10 constructed in accordance with the present invention and connection with a ballast discharge conduit 12 (only a portion of which is shown) through which a stream of ballast or the like flows in the direction shown, typically comprising an oily water stream. An oily water sample is withdrawn in a conventional manner (typically through a sample tap) via tubular or conduit line 14 at a location 16 in the conduit 12 and is passed through a constant pressure regulator 18 and then through the tubular line of conduit 20 into a sample manifold 22 constructed in accordance with the present invention. The regulator 18 insures constant velocity of any portion of the sample of oily water which contacts the tape by maintaining a constant pressure drop across the orifice which restricts the sample flow. A typical regulator comprises a variable orifice flow restrictor. Other devices which also are sufficient for this purpose include a constant-head tube with overflow or a pump with constant output pressure. At a point 24 located upstream from the sample withdrawal point 16, there is provided a flow sensor 26, which typically comprises a conventional orifice and pneumatic amplifier, for sensing the flow rate of the ballast discharge and producing an output pneumatic signal of 3 to 15 psi which is proportional to the rate of ballast discharge flow. The signal is coupled to a pneumatic positioner 28 (e.g. a control valve actuator) via conduit 30. The positioner 28 in turn is coupled through its output shaft 32 which is movable in an axial direction, to a movable vane 34 (see FIG. 2) which is positioned within the manifold 22. The control positioner causes the vane 34 to move axially such that the total oily water sample flow rate out of the manifold is proportional to the total ballast discharge flow rate. A belt of lipophilic tape 36 is pulled at a constant speed from a supply reel 38 (which rotates counter-clockwise) in a direction passing beneath the sample manifold 22 which is transversely located relative to the direction of tape movement, for depositing sample on the tape as discussed in detail hereinafter. The tape is collected and stored on a takeup reel 40 (also rotating counterclockwise) which in the preferred embodiment is located in a refrigerated container 42 which minimizes the deleterious effects of vaporization, oxidation and bio-degradation of the oil on the tape. As the tape traverses from the supply reel 38 to the takeup reel 40, it passes under the sample manifold 22, which directs oily sample water through all or a portion of the tape width dependent on ballast discharge rate. The percentage or portion of tape width contacted with the sample oily water is adjusted by means of the piston 34 (see FIG. 2) which as described above, is controlled by the pneumatic signal (from flow sensor 26) proportional to the flow rate of the ballast water being discharged. As the sample passes down through the tape, it is received in a funnel or chamber 44 located directly on the opposite side of the tape 36 below the sample manifold 22 and is discarded into a suitable storage or chamber 46.

As shown in FIGS. 1-4, the tape 36 is illustrated moving in the direction from right to left as seen in FIG. 1. The oily water sample enters the manifold 22 and falls through an open channel or slot 48 which is centrally located in the bottom wall of the manifold and is not covered by the moving piston or vane 34 as described in further detail hereinafter. The blockage member 34 as shown in the preferred embodiment comprises a piston which blocks more or less of the open channel 48 depending upon the extent to which the piston has been caused to move axially into the manifold 22 in response to the output of the pneumatic positioner 28. Alternatively, the positioner may comprise a control valve actuator or air piston controller. Thus, no sample will flow through that portion of the channel which is obstructed by the piston blockage member 34. For example, at maximum ballast discharge flow rate, the piston member 34 would be fully retracted, that is, substantially all the way to the right as shown in FIG. 2. The oily water sample enters the manifold and flows through substantially the entire channel 48 which has a width corresponding to that of the tape width, and therefore contacts the lipophilic tape passing thereunder for its full width. Conversely, when no ballast is being discharged, the sample flow blockage member 34 would be fully extended, that is, the entire channel above the tape is blocked, thus, preventing any of the sample from flowing through the manifold onto the tape. There is a provision for a flow of sample which does not contact the tape and thus continuously flushes the sample line (for example, as shown by the portion of sample flow nearest the sample inlet line 20 in FIG. 4). As shown in the illustration of the preferred embodiment, the blockage member 34 is approximately two-thirds extended, thereby allowing oily sample water to contact the one-third of the moving tape, which corresponds to a ballast discharge rate of about one-third maximum flow rate which is assumed for purposes of this illustration. As the oily water sample flows through the tape in the area where the blockage member has been withdrawn, the funnel 44 (FIG. 1) will collect it and suitably dispose of it. As the oily water sample flows into the manifold its velocity is such as to cause it to distribute axially inward from its inlet end and thereby pass through the uncovered portion of the channel.

Figure 5:
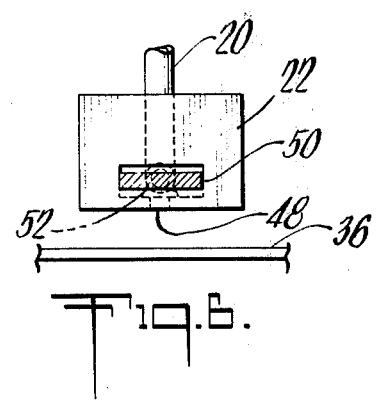
FIG. 5 is a view similar to that of FIG. 2 only showing an alternate construction of the sample manifold.

An alternate arrangement and modification to the preferred embodiment of FIGS. 1-4 is shown in FIGS. 5-7. According to this latter version of the invention which employs the same overall arrangement, the sample manifold 22 in the bottom wall thereof is provided with a plurality of axially-aligned openings or apertures 48 which extend from the interior of the manifold through the bottom wall, such that sample flow passes through those openings which are not covered by a vane or blockage member which is illustrated in FIGS. 5-7 as comprising a planar or flat vane 50 and is connected at one end to the positioner output shaft 32. Each of the holes typically is fitted with a means such as a rubber grommet 52 in order to provide a fluid tight seal with the overlying vane 50 for shutting off any flow through those holes. The flat vane 50 is made from any suitable material (e.g. plastic) and is in sliding engagement with the tops of the grommets 52, and is sufficiently biased, for example, by the sample water pressure above the vane or appropriately arranged resilient means in the downward direction (toward the bottom wall) so as to form a fluid tight seal with those holes which it overlies. The vane is of sufficient width so that if it traverses slightly to either side of its preferred axial path the openings still will be covered. Also, the seal could be associated with the vane instead of with each opening.

Figure 8:
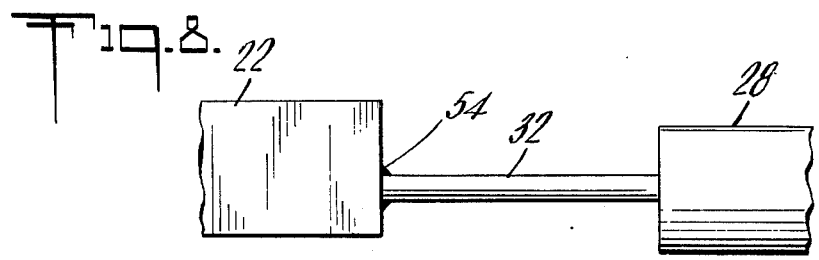
FIG. 8 is another embodiment of the present invention.
Figure 9:
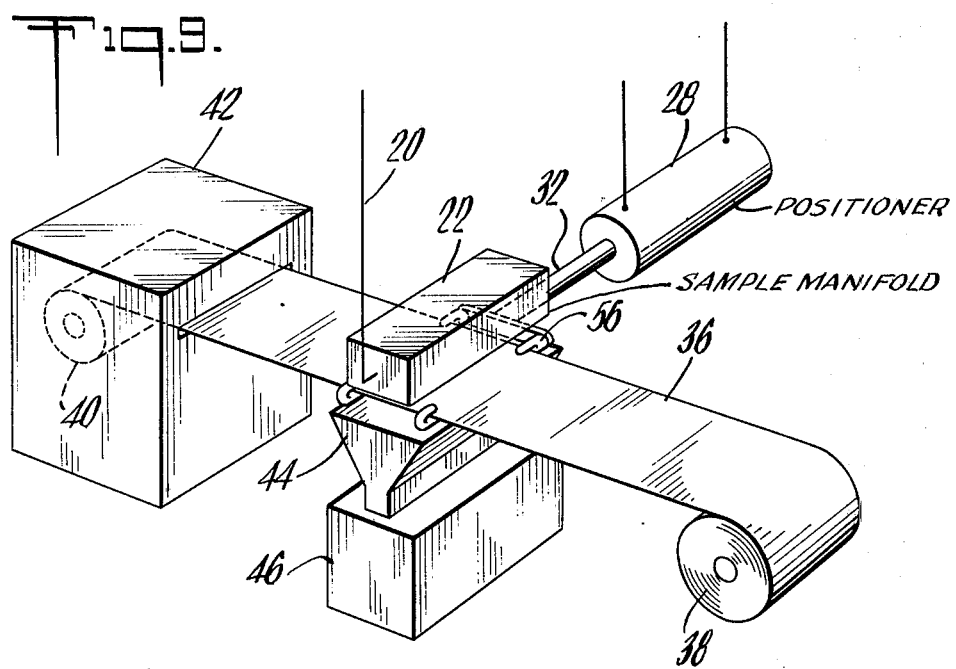
FIGS. 9 and 10 are further embodiments of the present invention.
Figure 10:
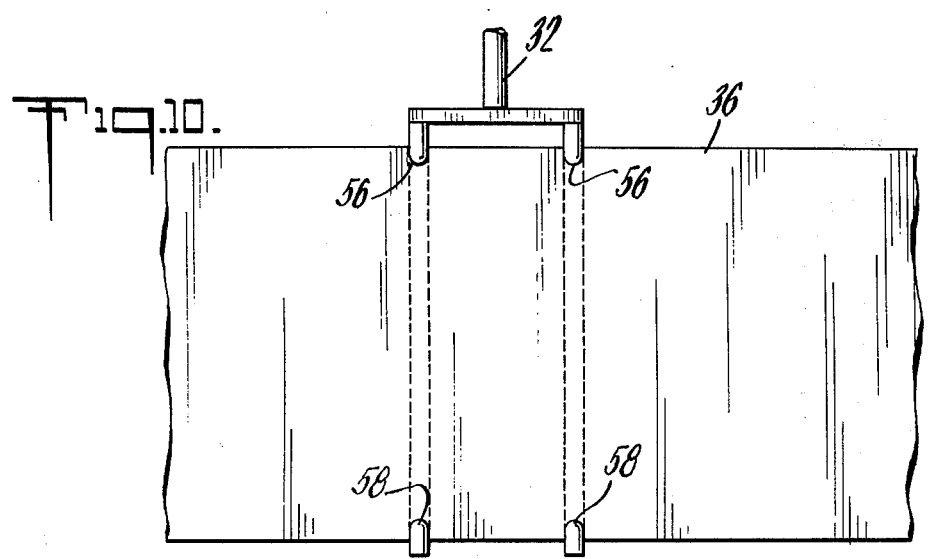

Further alternative embodiments can be constructed similar to the arrangement shown in FIGS. 5-7, except without a vane 50. Instead, the positioner output shaft 32 is connected directly (e.g., by welding, nuts and bolts, etc.) to the sample manifold 22 as shown at 54 in one embodiment (see FIG. 8) or to guides 56, 58 on either side of the tape 36 and directly below the sample manifold 22 in the other embodiment (see FIG. 9), similar to the ribbon supports for a typewriter ribbon. In the latter embodiment the tape is made sufficiently slack so that it can be moved sidewise, i.e., transversely relative to the manifold, by the positioner shaft 32. In either case, the sample would continuously flow at constant velocity through all of the channel or openings 48 and the positioner output shaft 32 would displace in an axial direction (i.e., transverse to the direction of tape movement) the relative vertical alignment between the sample manifold 22 and the tape 36 in a direct proportion to the ballast discharge rate such that at the maximum discharge rate, the entire tape width would be contacted with sample (coextensive alignment); at one-third of the maximum discharge rate, one-third of the tape width would be contacted with sample (offset alignment); and when there is no ballast water being discharged then none of the flowing sample would contact the tape (non-alignment).

The foregoing combination of nozzle, blockage member and moving lipophilic belt provides the present oil pollution compliance monitor with capability for continuously recording both oil concentration and total oil being discharged. This is possible because the amount of oil retained in any spot or specific location which has been contacted by the oily water sample on the tape is directly proportional to the oil concentration discharged by the tanker at the time that spot was contacted by the sample. The amount of oil adsorbed laterally across the tape width is proportional both to concentration and ballast discharge flow rate (because the movement of the blockage member is proportional to ballast flow rate) and therefore, is directly proportional to the total amount of oil discharged from the ship at the time that the particular tape width is contacted with the sample. Since the tape belt moves at a constant speed during the ballast discharge, the total oil in the belt is directly proportional to the total oil discharged from the tanker during the ballast discharge operation.

By analysis of the oil concentration discharged at any particular instant, the total oil discharged at any instant, and liters per mile of oil discharged at any instant and total oil discharged during the voyage can be readily accomplished by removing the tape belt from the ship after the voyage is completed, taking the belt to a laboratory and proceeding as outlined below.

To find the oil concentration at any instant in time, one would first define the belt position which corresponds to the instant in question and carefully remove a very tiny portion of the belt at that location. To facilitate this, the belt can be provided with markers along its length which would correspond to location and/or time in a particular voyage. Then, a solvent extraction of that removed portion followed by standard laboratory analysis will yield total oil in that portion of the belt. By combining the analyzed oil content with sample flow rate, belt speed and the width of the analyzed portion, the oil concentration in the oily water sample which contacted the analyzed portion of the belt can be determined.

If the following parameters are defined,

PPM in Solvent = PPM of oil measured in the laboratory analysis
Volume = Volume of solvent used in the laboratory to extract the oil from the tape section
Area = Area of tape section analyzed
Weight = Weight of tape section after oil is extracted
Length = Dimension of tape section in direction of tape transport movement
Velocity = Velocity of tape transport
Flow = Sample water flow rate through tape section
$K_n$ = Constants appropriate to the conditions described then a suitable formula for obtaining oil concentration would be:

$$\text{PPM Discharged at Time of Interest} = \frac{(\text{PPM in Solvent}) \times (\text{Volume}) \times (\text{Velocity}) \times (K_1)}{(\text{Area}) \times (\text{Flow})} \quad (1)$$

Assuming that Velocity and Flow are also constant in this monitor, then the above equation simplifies to:

$$\text{PPM Discharged at Time of Interest} = \frac{(\text{PPM in Solvent}) \times (\text{Volume}) \times (K_2)}{(\text{Area})} \quad (2)$$

If the tape has uniform density and thickness, then the difficult to measure area of a small piece of tape can be replaced by the easier to measure parameter of weight:

$$\text{PPM Discharged at Time of Interest} = \frac{(\text{PPM in Solvent}) \times (\text{Volume}) \times (K_3)}{(\text{Weight})} \quad (3)$$

Finally, if the laboratory analysis procedure is standardized such that the size and weight of the piece of tape were reproducible (as would be the case if a special punch were used to remove the piece), then the volume of solvent used in analysis could also be standardized such that the product of all non-variable factors would be unity and EQ 3 would further simplify to:

$$\text{PPM Discharged at Time of Interest} = \text{PPM in Standard Solvent Volume}_1 \quad (4)$$

To determine the total rate of oil discharged at any particular instant, the procedure as outlined above is followed, except that a thin section of the total belt width is analyzed. Total rate of oil discharged then is found by the following equations:

$$\text{Rate of Oil Discharged at Time of Interest} = \text{PPM Discharged at Time of Interest} \times \text{Rate of Oily Water Discharged} \quad (5)$$

$$\text{Rate of Oil Discharged at Time of Interest} = \frac{(\text{PPM in Solvent}) \times (\text{Volume}) \times (K_4)}{(\text{Length})} \quad (6)$$

$$\text{Rate of Oil Discharged at Time of Interest} = \frac{(\text{PPM in Solvent}) \times (\text{Volume}) \times (K_5)}{(\text{Weight})} \quad (7)$$

$$\text{Rate of Oil Discharged at Time of Interest} = \text{PPM in Standard Solvent Volume}_2 \quad (8)$$

The liters per mile of oil discharged in any instant is obtained by dividing the above total oil per unit of time by the ship's speed which can be obtained from the ship's log at the time in question.

Finally, the total oil discharged over the complete voyage is obtained by proceeding as in the analysis of oil concentration at any instant, except that the solvent extraction is performed on the entire belt. Thus, $$\text{Total Oil Discharged Over Voyage} = (\text{Rate of Oil Discharged}) \times \text{Time Duration of Discharge} \quad (9)$$

$$\text{Total Oil Discharged Over Voyage} = (\text{PPM in Solvent}) \times (\text{Volume}) \times (K_6) \quad (10)$$

$$\text{Total Oil Discharged Over Voyage} = \text{PPM in Standard Solvent Volume}_3 \quad (11)$$

The only time that the foregoing analysis would necessarily have to be performed, would be if the tanker had to prove that it had not violated international limitations in its ballast discharge operations.

In the subject invention, there are no electronic components provided which makes the monitor intrinsically safe and, therefore, it can be installed at any convenient location on board a tanker. Ballast discharge flow rate range-ability problems easily can be solved by combining multiple installations which respond to different flow ranges, i.e., 0–6000 tons per hour for ballast water discharges and 0–200 tons per hour for stripping pump discharges. Finally, as mentioned before, according to the invention it is possible the tape can be reeled into a tamperproof locked box which would be opened only by authorized personnel, thus providing the necessary proof of compliance or non-compliance, as the case may be, with regulations.

While a particular embodiment of the invention has been shown and described and various modifications thereof have been suggested, it will be understood that the true spirit and scope of the invention is set forth in the appended claims which embrace other modifications and embodiments which will occur to those of ordinary skill in the art. For example, while the monitor is disclosed for use with ballast discharge from a tanker it also could be used in any situation involving continuous or periodic discharge of potentially contaminated water and the like, such as from a refinery or an offshore drilling platform. Also, while oil is the pollutant of concern in the preferred embodiment, other pollutants such as particulates, dissolved solids, heavy metals, etc. could be of concern in other instances. Furthermore, this technique can be readily adapted for use in recording concentration, rate of discharge and total amount of pollution from gaseous effluents such as smokestacks, exhausts, etc.

Having thus described the nature of the invention, what I claim herein is as follows:

1. A pollution compliance monitor system for monitoring and recording pollutant discharged over a specified period in a flowing discharge stream comprising, in combination: a belt of tape movable at a constant speed from a supply reel to a takeup reel; sample manifold means situated above said tape for receiving and directing a sample of the discharge stream at a constant velocity through said tape as a function of the flow rate of said discharge stream; flow sensor means for sensing the flow rate of said discharge stream; positioner means responsive to the sensed flow rate for controlling the amount of discharge sample to contact said tape in proportion to the rate of flow of said discharge stream.

2. The system of claim 1 including blockage means in said sample manifold means connected with said positioner means and operable in response to the sensed flow rate of said discharge stream by said sensor means for regulating the amount of sample contacted with said tape.

3. The system of claim 2 wherein said manifold means includes in the bottom thereof a channel opening extending for substantially the length thereof, siad blockage means connected with said sensor means and positioned in overlying relation with respect to said channel as a function of sensed flow rate.

4. The system of claim 2 wherein said blockage means comprises a flat vane movable in an axial direction in response to said flow sensor.

5. The system of claim 2 wherein said manifold means includes a plurality of openings extending for substantially the length thereof and seal means disposed between said blockage means and said openings for providing a fluid tight seal therebetween when said blockage means is in overlying relationship with at least certain of said openings.

6. The system of claim 3 wherein said seal means comprises rubber grommets associated with each of said openings disposed for fluid sealing relationship with said blockage means.

7. The system of claim 1 wherein said positioner means comprises a pneumatic signal controller for providing a pneumatic output signal proportional to said stream discharge flow rate.

8. The system of claim 1 wherein said sample manifold means is disposed transversely of the direction of movement of said tape.

9. The system of claim 2 wherein said blockage means comprises a flat vane member disposed in a plane substantially parallel to said tape.

10. The system of claim 1 including pressure regulator means located between said sample manifold means and the discharge stream for directing a uniform sample flow rate of said sample to said sample manifold means.

11. The system of claim 3 wherein said blockage means comprises an axially movable piston disposed for preventing sample flow through said channel in proportion to the stream discharge flow rate sensed by said flow sensor means.

12. The system of claim 1 including means located below said belt for receiving sample flow passing therethrough.

13. The system of claim 1 wherein said belt of tape comprises a lipophilic tape.

14. The system of claim 3 wherein said channel is centrally located of said manifold means.

15. The system of claim 1 wherein said positioner means controls the relative vertical alignment by said tape and said sample manifold means as a function of stream discharge rate.

16. The system of claim 15 wherein said positioner means is connected directly to said sample manifold means for moving the latter transversely by said tape as a function of stream and discharge rate.

17. The system of claim 1 wherein said positioner means is connected directly to said sample manifold means.

18. The system of claim 1 including means for connecting said positioner with said tape for moving said tape transversely relative to said sample manifold means.

19. The system of claim 1 wherein said positioner means is connected for providing relative transverse movement between said tape and said sample manifold means.

20. The system of claim 1 including guide means operably associated with said tape for permitting said tape to freely pass therethrough in its direction of normal movement; means connecting said guide means to said positioner means for moving said guide means and said tape in a direction transverse to the direction of normal movement of said tape.

21. A method of monitoring and recording the rate of pollutant and total pollutant discharged over a specified period in a discharge stream, comprising the steps of:
  a. monitoring at a first location the rate of flow of said discharge stream;
  b. providing a signal representative of monitored rate of flow;
  c. extracting a sample from said discharge stream;
  d. contacting a moving belt of tape which is capable of absorbing pollutant within said sample as a function of said signal, whereby the pollutant concentration and pollutant discharge flow rate can be determined.

22. The method of claim 17 including the step of:
  e. contacting only a portion of the width of said tape as a function of said signal.

* * * * *

UNITED STATES PATENT OFFICE
CERTIFICATE OF CORRECTION

PATENT NO. : 3,985,020
DATED : October 12, 1976
INVENTOR(S) : James O. Moreau

It is certified that error appears in the above-identified patent and that said Letters Patent are hereby corrected as shown below:

In the claims, column 10, line 17, change "17" to --21--.

Signed and Sealed this

Twenty-fifth Day of January 1977

[SEAL]

Attest:

RUTH C. MASON
*Attesting Officer*

C. MARSHALL DANN
*Commissioner of Patents and Trademarks*